United States Patent [19]

Kraegen et al.

[11] Patent Number: 4,475,901

[45] Date of Patent: Oct. 9, 1984

[54] APPARATUS FOR IMPROVING BLOOD SUGAR CONTROL IN DIABETICS

[75] Inventors: Edward W. Kraegen, Bondi Junction; Leslie Lazarus, St. Ives; David J. Bell, Strathfield; Donald J. Chisholm, Roseville, all of Australia

[73] Assignees: The Garvan Research Development Ltd.; The Commonwealth of Australia, both of Australia

[21] Appl. No.: 318,775

[22] Filed: Nov. 6, 1981

[51] Int. Cl.³ .............................................. A61M 5/00
[52] U.S. Cl. .................................... 604/67; 128/419 P; 604/66
[58] Field of Search ............ 128/213 R, 214 R, 214 E, 128/214 F, 260, 419 P; 604/65, 66, 67

[56] References Cited

U.S. PATENT DOCUMENTS 4,078,562  3/1978  Friedman ............................ 128/213
4,146,029  3/1979  Ellinwood, Jr. ................. 128/419 P

OTHER PUBLICATIONS

Martin et al., "Normalization of Insulin Delivery to Diabetics by Pulsed Insulin Infusion"; IEEE Transactions on Biomedical Engineering, Mar. 1977, pp. 116-121.

Albisser, "Devices for the Control of Diabetes Mellitus", Proceedings of the IEEE, vol. 67, No. 9, Sep. 1979, pp. 1308-1320.

Primary Examiner—Edward M. Coven
Attorney, Agent, or Firm—Ladas & Parry

[57] ABSTRACT

There is provided an apparatus to improve control of blood sugars in diabetics. The apparatus comprises an infusion means and a control means which controls the infusion rate of one or more diabetics control liquids. The control means comprises a basal rate means to control infusion of the liquid according to an assessed basal metabolic requirement and a non-basal rate means to control infusion of the liquid at one or more levels of metabolic activity. The control means is preferably adapted to receive patient data to vary the infusion of the liquid accordingly.

10 Claims, 6 Drawing Figures

APPARATUS FOR IMPROVING BLOOD SUGAR CONTROL IN DIABETICS

The present invention is directed to an apparatus which will improve control of blood sugars in diabetics.

At the present time there are two major problems that face the insulin-dependent diabetic. Firstly there is the problem of avoiding particularly high or particularly low blood sugar levels which in themselves will cause incapacity. In some diabetics, this is not too difficult, but other "brittle" diabetics do have a considerable amount of trouble avoiding hyperglycaemic or hypoglycaemic (insulin) reactions. An "artificial pancreas" which would maintain euglycaemic levels would be a great blessing for diabetics, especially these brittle diabetics.

However, there is a far greater problem which applies to all insulin-dependent diabetics. That is, the problem of long term complications affecting the nerves, blood vessels, heart, kidneys and eyes. There is much evidence to suggest that if blood glucose levels could be controlled in the ideal range by an artificial pancreas that these worrying complications could be substantially reduced or ameliorated.

Other recent developments have already made some improvements in the life of the diabetic. Pure insulins have abolished some of the reactions to insulin treatment, particularly those of an allergic type. Measurement of glycohaemoglobins (glucose altered haemoglobin) can now be performed in many clinics and may give a better overall idea of diabetic control than simple urine testing and occasional blood glucose estimations. Frequent blood glucose measurements performed at home by the diabetic have also been a definite advance in helping the diabetic and his physician know more about his blood sugar level, and thus allow better adjustment of insulin dosage. However, none of these developments represent a means by which the diabetic can achieve "metabolic normality".

Two previous approaches to regulation of blood glucose in diabetes as alternatives to insulin injections have been proposed; pancreatic tissue implantation and apparatus that controls blood glucose concentration by means of feedback-control or preprogrammed insulin delivery. The mechanical devices can be divided into two categories: closed-loop systems, in which insulin or other substances are given in response to a measured change in blood glucose, and open-looped systems, in which insulin is delivered in a preprogrammed manner independent of changes in blood glucose.

A closed-loop, insulin delivery system or a pancreatic cell simulator consists of three basic components: a glucose sensor, insulin or drug delivery pump and a controlling device that regulates the administration of insulin or other drug based on the measured amount of glucose. Ideally, such a system would be small enough to offer the potential for implantation or prolonged-portable use. No such ideal device is currently available, primarily because neither glucose sensors nor insulin delivery pumps that are sufficiently small and reliable enough for long term use in vivo have been developed. Furthermore, even if these two components were available, the problem of operating the controlling device to maintain blood glucose concentrations in ambulatory insulin-dependent diabetics within the narrow, physiological range seen in non-diabetics, still remains. The clossed-loop artificial pancreas basically responds to changes in blood glucose levels from minute to minute, analogous to the response of a healthy pancreas. However, the closed-loop systems have inherent problems. Early studies showed that a five to ten minute delay between blood withdrawal and glucose measurement introduced an inherent delay in closed-loop control. This delay necessitated operation of the controlling device so that insulin administration was based on an extrapolated predicted glucose concentration. This prediction was a function of the actual glucose concentration and its rate of change over the previous few minutes. Moreover, the necessity for a glucose sensor in the closed-loop systems inhibits the potential of these systems for miniaturization.

Open-looped insulin delivery systems attempt to control blood glucose concentrations in diabetics whose daily insulin requirements are predetermined during a previous period of management. Basically, insulin is infused so as to attempt to reproduce the pattern of diurnal plasma insulin concentrations in a non-diabetic's plasma before and after meals. Blood glucose is not measured but instead the insulin infuser is directed to deliver insulin to the diabetic according to preplanned instructions. A fundamental problem arises in the production of a commercially practical device, however, that different rates of infusion are required for different anticipated basal metabolic requirements and food ingestion levels of the patient. Furthermore, since the actual levels may well differ from the anticipated levels, some method of variation of these rates will result in a better approximation to the normal physiological response.

It is an object of the present invention to provide an improved infusion system which overcomes, or substantially ameliorates, the abovementioned disadvantages.

According to one aspect of the present invention, there is disclosed an infusion system comprising an infusion means and control means connected thereto to thereby control the operation of said infusion means, said infusion means comprising a first pump connected between a first diabetic control liquid reservoir and a tissue access system connected to the body of the patient whereby diabetic control liquid from said reservoir is infused into said body; and said control means comprising basal rate means to operate said pump to a base rate corresponding to an anticipated basal metabolic requirement of said patient, and meal rate means to increase the operation of said pump by predetermined amounts over a predetermined time corresponding to anticipated ingestion of food by said patient, both said basal rate means and said meal rate means being adjustable to select one of a plurality of rates corresponding to different anticipated levels of basal metabolic requirements and food ingestion.

In a particularly preferred embodiment of the present invention the system receives patient data at predetermined intervals, preferably blood glucose levels, and the pump rate is varied responsive to said data. Preferably the blood glucose levels of the patient are entered into the control means at predetermined levels and the control means assimilates this data and varies the pump rate accordingly. In this particular embodiment the hybridisation of the open loop system and the closed loop system allows more variable and adaptable control of blood sugar in diabetics.

Preferably, the present invention also includes means by which either insulin or dextrose or both, can be infused. In addition, the ability to adjust the basal and meal rates also permits adjustment according to the degree of insulin sensitivity of the patient (e.g. obese, child) concerned.

In another preferred embodiment of the present invention, there is included means by which intravenous nutrition can be provided in the form of an infusible solution of dextrose, protein hydrolysates and other solutes.

Although the apparatus of the present invention finds a most useful application in the treatment of diabetes in man, the apparatus also lends itself to being a useful analytical tool to research the mechanism of such disorders, especially in conjunction with the glucose clamp technique, which technique is described by DeFronzo, Ralph A., Jordan D. Tobin, and Reubin Andres, in "Glucose clamp technique: a method for quantifying insulin secretion and resistance." Am. J. Physiol. (237(3): E214–E223, 1979 or Am. J. Physiol.: Endocrinol. Metab. Gastrointest. Physiol. 6(3):E214–E223, 1979.

This technique is subdivided into two techniques: the hyperglycaemic clamp and euglycaemic clamp techniques which promise reproducible, physiological methods of quantifying cell sensitivity to glucose and tissue sensitivity to insulin. In the first technique the plasma glucose concentration is maintained at an hyperglycaemic plateau by controlled infusion of dextrose first by infusion of a priming dose to raise the glucose levels in plasma and in extravascular glucose compartments to a predetermined level, and secondly by maintenance doses at predetermined intervals thereafter. The plasma insulin response is monitored at the same time by blood sampling.

In the euglycaemic insulin clamp technique, a steady state plateau of hyperinsulinemia is maintained by controlled infusion of insulin. At the same time, hypoglycaemia is prevented by application of the glucose clamp technique, in order to maintain the subject at basal plasma glucose levels.

The above techniques in conjunction with the apparatus of the present invention provide a valuable tool to study glucose homeostasis irregularities, by providing an accurate and reliable means of controlling infusion of both glucose and insulin to achieve predetermined plasma glucose levels.

A preferred embodiment of the present invention will be described by way of example only and with reference to the accompanying drawings in which.

Figure 1:
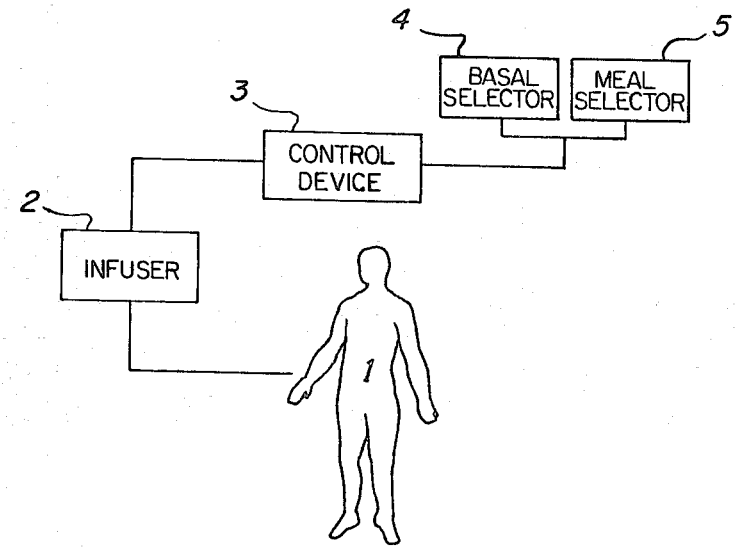
FIG. 1 is a block diagram of a basic open-loop system.

Referring to FIG. 1, the open-loop system of the preferred embodiment comprises an insulin infuser 2 which supplies insulin to the patient 1. The rate of supply of insulin is controlled by a control device 3 which operates at either one of several base rates or one of several meal rates according to whether basal rate selector 4 or meal rate selector 5 is respectively selected.

The insulin infuser 2 of FIG. 1 comprises a pump together with an insulin reservoir (not illustrated). The pump is operated by a D.C. motor and gearbox which rotates an eccentric cam to compress a tube connecting the reservoir to the patient and thereby causing insulin to be delivered to the patient 1.

The outlet of the pump is attached to a tissue access system by which route the insulin and possibly in addition, a suitable source of glucose, is administered. The infuser 2 is capable of insulin delivery over a tenfold range to provide a range of basal infusion rates and higher rates for post prandial delivery. Post prandial insulin delivery should be given in a time profile corresponding to a normal metabolic post prandial response.

Figure 2:
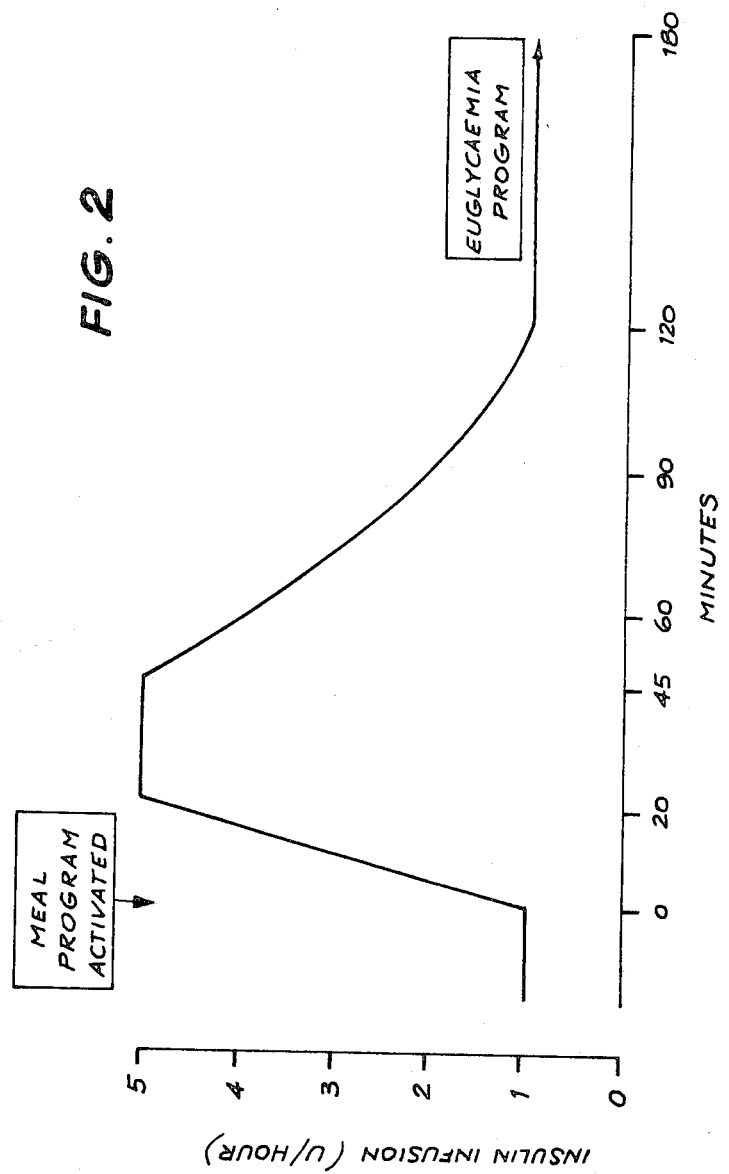
FIG. 2 is a graph of the insulin infusion rate against time for the meal profile used in the method and apparatus of the present invention.

FIG. 2 illustrates a preferred insulin infusion rate which will simulate the normal pancreatic response to ingestion of food, with a gradual return to the patient's basal infusion rate over the post prandial period of 3 to 4 hours. The infuser 2 is designed to have selectable basal infusion rates, preferably 3 rates, corresponding to normal, reduced and enhanced basal rates, which substantially respectively correspond to normal, reduced and enhanced physical activity of the patient.

The magnitude of these rates are predetermined from a spread of possible magnitudes by, or under the direction of, the patient's physician. The patient can then select approximate basal rates for overnight, day-time, exercise, etc., according to the patient's intended activity. A preferred safety feature for ambulatory patients is a safety device to prevent the patient (especially child patients) altering the basal rate.

Precise post prandial infusion rates (or infusion profiles) as a function of time for a particular patient will be set in advance by the physician according to the patient. Preferably, there is an optional facility of selecting a reduced meal profile which will deliver a preset smaller amount in insulin as an alternative to a normal meal profile to cater for unexpectedly reduced amounts of food intake.

There are three routes of insulin delivery through the tissue access system, namely the intravenous route, the subcutaneous route, and the intraperitoneal route. Preferably, the route of delivery will be the intravenous route, however, it will be clear to one skilled in the art that the tissue access system can utilize any one of the three possible routes.

There are of course special problems involved with intravenous infusion. One such problem is the prevention of entry or infection through the lumen of the catheter. This problem is substantially avoided by incorporating into the insulin and/or dextrose solutions one or more antimicrobial agents, and/or by introducing the solutions into the insulin/dextrose reservoir under aseptic conditions and/or establishing a permanent seal at the junction of the catheter and the pump outlet at the time of insertion of the catheter.

Moreover, attention is paid to the dressing of the skin wound at the point of insertion, and the catheter is securely immobilized close to this point of insertion through the skin. Strictly aseptic conditions are also adhered to when inserting the catheter. For operation for short periods of time i.e. less than 48 hours, a peripheral vein is a convenient site of entry for the catheter. However, for longer use, entry of the catheter to a cephalic or cubital vein is generally necessary. Alternatively, and preferably, a central vein such as the internal jugular, external jugular and one of the subclavian veins is selected for long term use.

Preferably, infusion rates of insulin and/or a substrate source of glucose are tuned such that pulses at intervals of less than 2 minutes are administered via the intravenous route.

The subcutaneous route suffers from the disadvantage of a delay in absorption of insulin. However, this route can be used to successfully control basal and post prandial hyperglycaemia provided sufficient allowance is made for the delay time in insulin reaction.

Irrespective of which route of insulin delivery is selected, the only part of the device to contact tissue will be the catheter. The catheter can be made from silicon rubber, such as medical grade silicon rubber available from Dow-Corning of the U.S.A. Alternatively, heparinised polymer catheters can be used for the intravenous route since this material may provide an additional safeguard against thrombogenesis.

The pump will vary according to whether the apparatus of the preferred embodiment is to be used with ambulatory patients, hence requiring a portable apparatus, or is to be used with hospitalised patients. For bedside use preferably, two modified, servo-controlled peristalic pumps (manufactured by IVAC Corporation of the U.S.A.) are used. These pumps include sophisticated safety features and are well accepted in intensive care units. The abovementioned pumps are for use in bedside apparatus whilst for ambulatory patients a smaller portable pump is used.

The insulin reservoir (not illustrated) of a portable system has a volume sufficient to maintain suitable dosages for patients up to seven days. One of the major problems with insulin is that its biological activity is vulnerable at normal body temperature (i.e. 37° C.) and this problem is a major barrier in the development of implantable devices. Hence, a reservoir with a supply of insulin lasting approximately 7 days is about the maximum volume able to maintain an active insulin supply.

Figure 3:
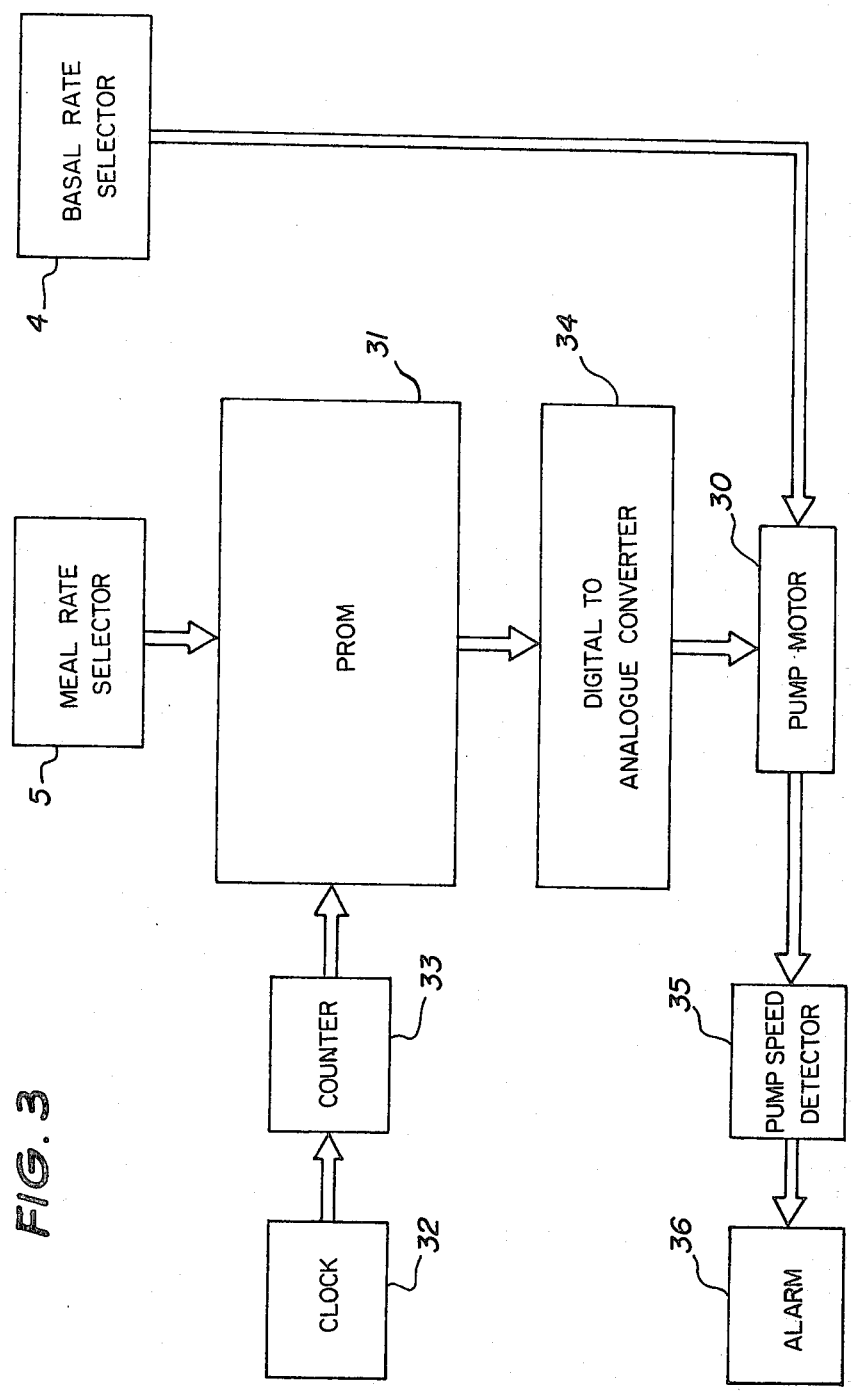
FIG. 3 is a block diagram of an infusion delivery system for use with ambulatory patients.

Turning now to FIG. 3, a block diagram of one embodiment of the apparatus of the present invention, which is for use with ambulatory patients, is illustrated. The pump motor 30 is supplied with D.C. voltages derived from two sources. One of these sources is the basal rate selector 4 which includes a switch able to be set at one of three positions so as to supply the pump motor 30 with one of three D.C. voltages. Accordingly, the basal rate selector 4 determines a base rate of rotation of the pump motor 30 and thus provides a base rate of insulin delivery for the pump.

In order to supply a second source of D.C. voltage to the pump motor 30 and thereby result in the pump delivering at an increased rate corresponding to a meal rate, the meal rate selector 5 is connected to a programmable read only memory 31 which, together with a clock 32, counter 33, and digital to analogue converter 34 comprises the control device 3 of FIG. 1.

The meal rate selector 5 includes a switch able to be set at either one of two positions thereby resulting in the PROM 31 assuming either one of two corresponding memory states. The clock 32 drives the counter 33 at a predetermined rate through a single cycle of the counter 33 thereby causing the contents of the PROM 31 to be read to the D to A converter 34. The D to A converter 34 converts the digital signal received from the PROM 31 into a D.C. voltage which changes as a function of time in accordance with the desired meal rate. This variable D.C. voltage when applied to the motor 30 increases the rate of operation of pump so as to increase the amount of insulin delivered thereby. In this way, the delivery rate of insulin is increased beyond the basal rate in order to provide the meal rate for the duration of the cycle time of the counter 33.

Preferably, a pump speed detector 35, of any convenient conventional construction, is also driven by the motor 30 so as to provide an indication of the rate of operation of the pump to an alarm 36. If the rate of operation of the pump falls below a first predetermined level, or rises above a second predetermined level, the alarm 36 is actuated thereby advising the patient that too little, or too much, insulin is being delivered to him. The patient is then able to take the necessary corrective action, for example, by replacing the batteries (not illustrated) which supply the motor 30 and the remainder of the circuitry, with electrical power.

Figure 4:
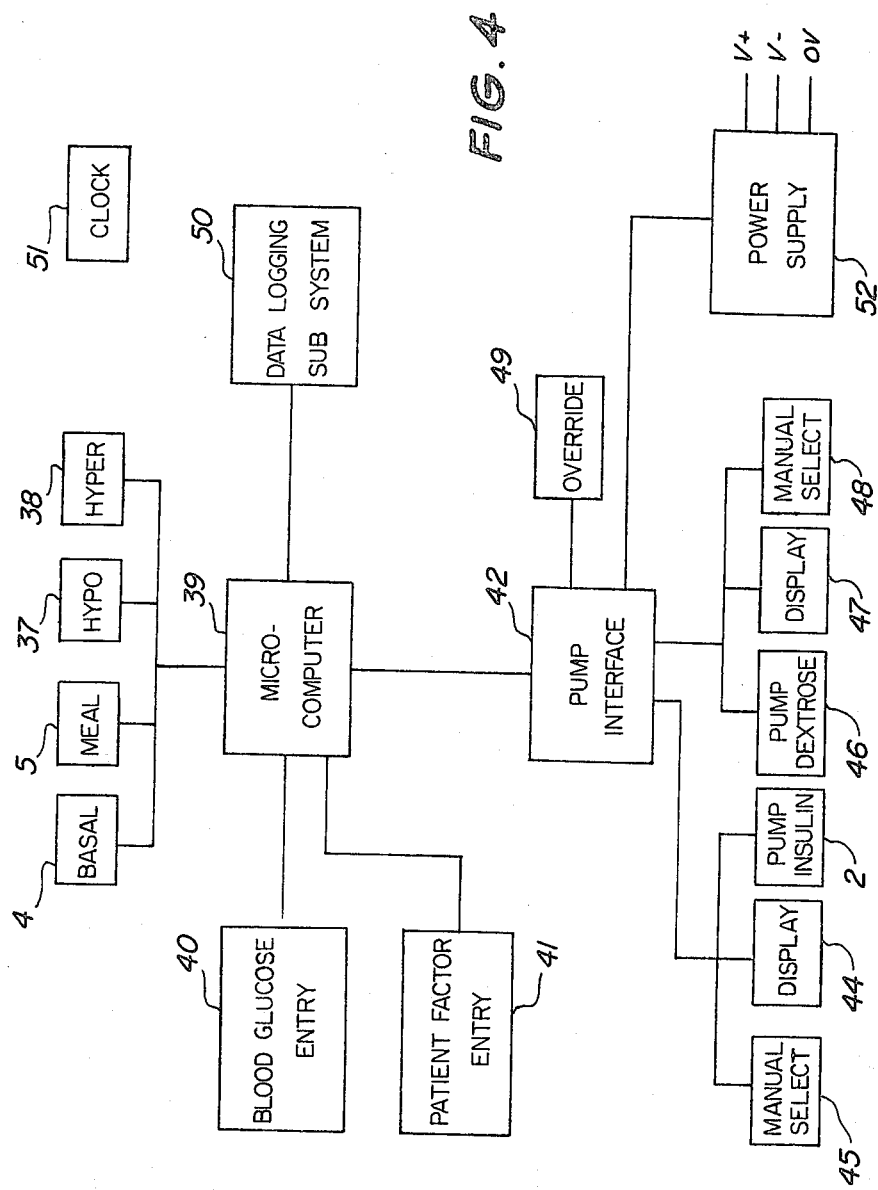
FIG. 4 is a block diagram of an alternative control device for an infusion system suitable for hospitalised patients.

As shown in FIG. 4, the bedside insulin delivery system consists of a micro computer 39 with associated peripheral inputs and outputs which correspond to the controller 3 of FIG. 1. The controller controls two pumps 2 and 46. One is the insulin infuser 2 of FIG. 2, whilst the second is used for infusing dextrose. Switches, preferably push-button switches, select different control programs corresponding to the basal and/or meal selectors of FIG. 1. Two additional control schedules are provided. These are used if the patient becomes hypoglycaemic or hyperglycaemic.

In another preferred embodiment, not illustrated, an additional control schedule is provided for intravenous nutrition, by which additional or increased quantities of dextrose can be infused, preferably in admixture with other nutrients such as protein hydrolysates.

The appropriate control schedule is selected by activating one of the basal 4, meal 5 hypoglycaemic 37, or hyperglycaemic 38, rate selectors. These are used to select different control schedules which are run on micro-computer 39. Blood glucose levels are entered using the blood glucose entry sub-system 40. The level is dialed on switches preferably thumbwheel switches, and a sample code is entered. Preferably, a light emitting diode is activated by the control schedules when a new blood glucose level is required. Preferably, the bedside insulin delivery system is adapted for better patient control by multiplying the insulin pump rate by a "patient factor", which can be entered so as to vary the insulin pump rate. Typically, this is in the range of 0.5 to 3.0, preferably, 0.8 to 2.5, and will vary, for example, with the obesity of the patient. In a preferred embodiment of the invention, the patient factor is entered by means of a thumbwheel switch 41.

The insulin 2, and dextrose 46 infusion pumps are controlled by a pump interface 42. The pump rates are loaded into a register in the interface 42 by the micro computer 39. Preferably, the pumps are IVAC pumps and their rate is determined by thumbwheel switches on the front panel of the pumps. An insulin manual select 45 and a dextrose manual select 48 can select the pump front panel rate as the actual pump rate. A reset switch 49 over-rides this selection and selects the prescheduled rate. It is preferable that two numeric displays 44 and 47 respectively display the insulin and dextrose pump rates. The data logging sub-system 50 is a printer with a keyboard and a set of switches. The switches are used to input the time of day to the system when it is switched on. The keyboard is used to activate the data logging printout on the printer. Preferably, the switches are thumbwheel switches. Eleven different events activate the data logging schedule. They are:

1. Start of basal rate
2. Start of meal rate
3. Start of hypoglycaemic rate
4. Start of hyperglycaemic rate
5. Alarm signal from either the insulin or dextrose pump
6. Request for a blood glucose sample
7. Activation of the manual rate on the insulin pump
8. Activation of the manual rate on the dextrose pump
9. Entering of a blood glucose level by an operator
10. Hourly Status
11. Reset of alarm condition, reset of the manual operation of the pumps.

Typically, the data schedule records the time of day, identifies the activating event, records the current blood glucose level, the time the blood sample was taken for the last blood glucose level, the number of drops of insulin infused, the number of drops of dextrose infused and the current patient factor. Upon request, this information is output to the printer.

Preferably, an independent clock 51 is also provided.

Preferably, in the event of mains power failure, the power supply 52 has a battery backup which allows the system to run for approximately one hour. The power supply has also circuitry to detect failure of the micro computer 39. The pump interface 42 is monitored and if the pump rates are not updated within a period of approximately one second, then power is disconnected from the micro computer 39.

In use, the basal control schedule is started by the basal rate selector switch 4. This sets a default value for the insulin and dextrose infusion pumps 2 and 46, reads the patient factor from the patient factor input switch 41 and requests the operator to enter via sub-system 40 a blood glucose level. Once the blood glucose level is entered, a pump rate is selected automatically from a look-up table contained in the micro-computer 39 and multiplied by the patient factor. Typically, approximately every three hours a new blood glucose level is requested. The pump rates are set at default levels until a new value of blood glucose is entered.

The meal control schedule runs for approximately three hours and a look-up table contained in the micro-computer 39 contains the meal profile as shown in FIG. 3. Typically, about every two minutes a new pump rate is selected from the look-up table depending on the time. The insulin pump rate is multiplied by the patient factor which is read when the schedule is selected.

If the hypoglycaemic rate selector 37 is activated, an increased amount of dextrose is pumped to the patient for a predetermined period of time whilst the insulin rate is decreased. Preferably, the dextrose pump rate increases to 75 drops per minute, and the insulin pump rate drops to 1 drop per minute for approximately 10 minutes only.

If the hyperglycaemic rate selector 38 is activated, the insulin pump rate will be increased whilst the dextrose pump rate is reduced. Preferably, the insulin pump rate is increased to about 48 drops per minute, whilst the dextrose pump rate drops to about 1 drop per minute for a predetermined time period of approximately 1 hour.

When the meal, hypoglycaemic and hyperglycaemic control schedule have expired, the basal control schedule is substituted.

Figure 5:
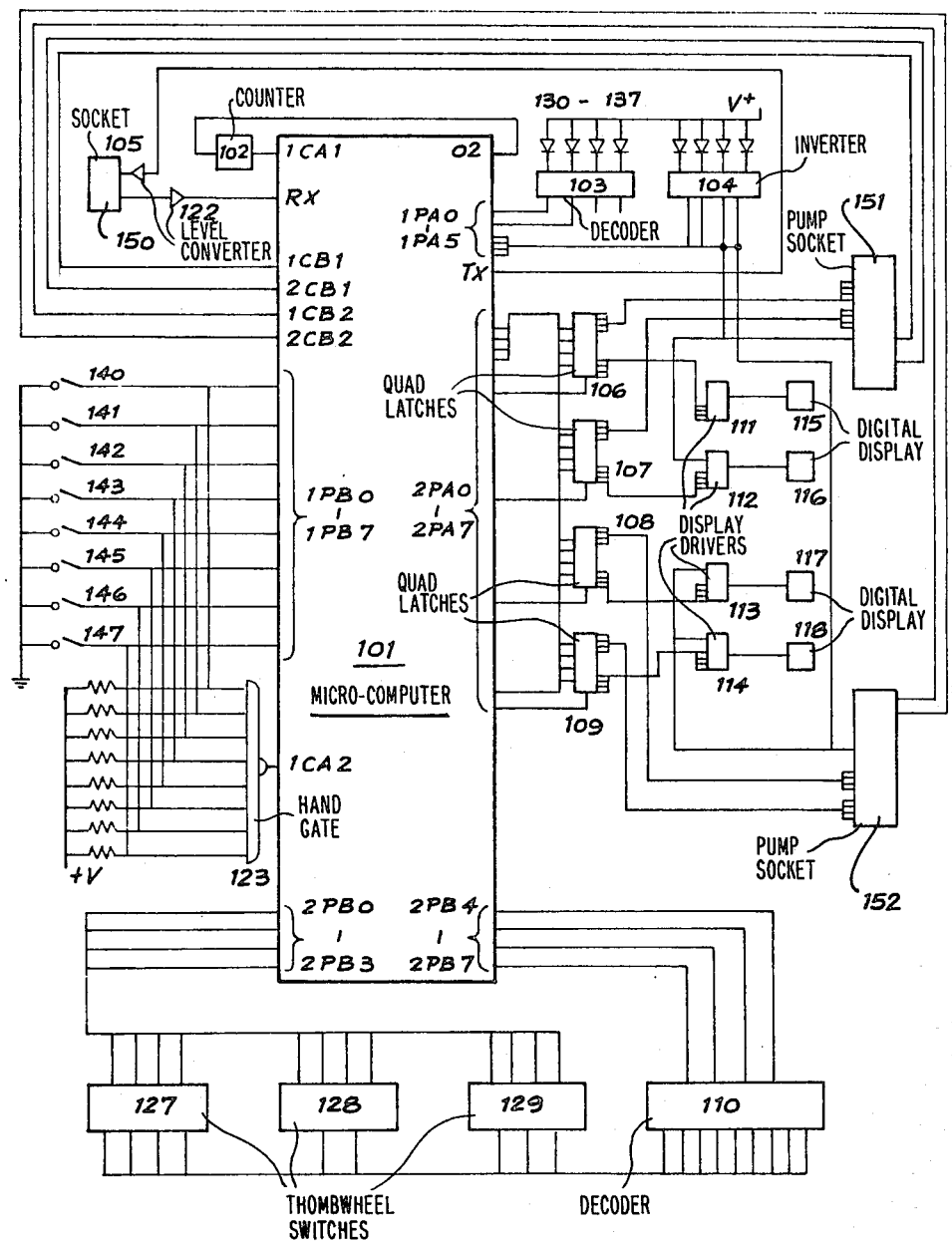
FIG. 5 is a schematic circuit diagram of the system of FIG. 4.
Figure 6:
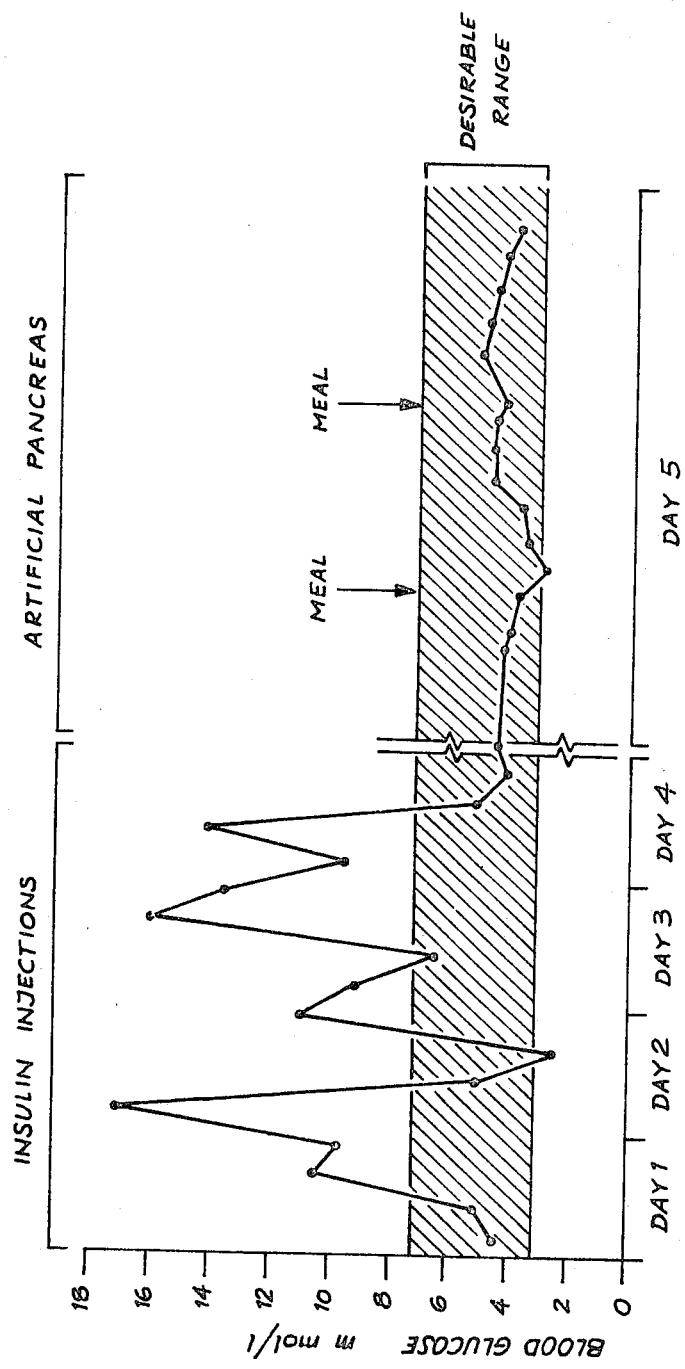
FIG. 6 is a graph of blood glucose as a function of time which shows the improved control of blood glucose possible in a "brittle" or "hard to control" patient using continuous delivery of insulin subcutaneously in accordance with the preferred embodiment.

The circuit used to carry out the above functions is illustrated in FIG. 5 and comprises a micro-computer 101 to which various other integrated circuits are connected.

Contained within the micro-computer 101 are two peripheral interface adaptors each of which has 20 input/output lines made up from two 8 bit input/output ports PA0–PA7, PB0–PB7 and four interrupt control lines CA1, CA2, CB1 and CB2. Also contained within the micro-computer 101 is an erasable programmable read only memory (EPROM).

An internal two phase clock 02 is contained within the micro-computer 101 and the clock output is passed to a 14 bit binary counter 102 which produces an output having a period of 14.187 seconds and which is applied as an input to the interrupt control line 1CA1. This arrangement functions to provide an internal time keeping arrangement with the micro-computer 101 which effectively enables it to ascertain the time of day and hence the elapsed time after a blood glucose result has been entered or after the meal button has been pushed.

Two outputs 1PA0 and 1PA1 are connected to a 4 bit serial input to 10 bit parallel output decoder 103 to which 4 light emitting diodes (LED's) 130 to 133 are connected to the four least significant output bits. These four LED's respectively indicate whether the basal, meal, hypoglycaemic or hyperglycaemic rate schedules have been selected and are running. In addition, further outputs 1PA2 to 1PA5 are connected to a hex inverter 104 in order to activate selected ones of LED's 134 to 137 which respectively indicate that a blood glucose sample is due to be obtained by the operator, and an alarm situation has arisen, that dextrose or glucose is being applied at a manual rate, and that insulin is being applied at a manual rate.

Furthermore the outputs 1PA4 and 1PA5 are each used to blank four seven segment digital displays 115 to 118 and their respective segment display drivers 111 to 114 inclusive. In addition, the outputs 1PA4 and 1PA5 provide an automatic/manual control signal to the modified IVAC pumps which are respectively connected to pump sockets 151 and 152.

Data logging is achieved by means of an asynchronous communication interface adaptor (ACAI) contained within the micro-computer 101 and which permits a teletype machine to be controlled via transmit and receive lines TX and RX. The signals from these lines are passed via two level converters 105 and 122 and thence to the socket 150 for the teletype machine. The level converters 105 and 122 convert the signal levels between that produced/required by the micro-computer 101 and that produced/required by the teletype machine.

The pump rate for the insulin pump (not illustrated) connected to socket 151 is determined by quad latches 106 and 107 whilst the pump rate for the dextrose pump (not illustrated) connected to socket 152 is determined by quad latches 108 and 109. The data for the latches 106 to 109 inclusive is provided from output lines 2PA0 to 2PA3 whilst the data is clocked into the latches 106 to 109 by output lines 2PA4 to 2PA7 respectively. The outputs from latches 106 and 107 are connected to the socket 151 for the insulin pump whilst the output of latches 108 to 109 is connected to the socket 152 for the dextrose pump. The logical complement of the output of latches 106 to 109 provides an input to the binary coded decimal to seven segment display drivers 111 to 114 respectively. Thus the actual pump rates which are determined by the voltages applied to the pump sockets 151 and 152 respectively are displayed by means of displays 115 to 118 respectively. Displays 115 and 116 each display one digit of the two digit rate of the insulin pump connected to socket 151 whilst displays 117 and 118 display one digit of the two digit rate of the dextrose pump connected to socket 152.

Eight push button switches 140 to 147 respectively are provided in order to initiate certain functions. Each switch 140 to 147 is connected to a corresponding input 1PB0 to 1PB7 respectively and, via a pull-up resistor to a supply voltage and a corresponding input of an eight input NAND gate 123. The output of NAND gate 123 is applied to an interrupt input 1CA2.

The functions provided by the eight push button switches 140 to 147 are entry of glucose sample, manual delivery of insulin, manual delivery of dextrose, alarm, start of hypoglycaemic schedule, start of hyperglycaemic schedule, start of meal schedule and start of basal schedule respectively.

Thus, switch 140 is used to indicate to the micro-computer 101 that a new blood glucose level has been entered into thumbwheel switch 129 whilst the switches 141 and 142 are used to switch the insulin and dextrose pumps from automatic to manual mode respectively. The switch 143 is used to clear the alarm display.

Operation of any one or more of the switches 140 to 147 enables the NAND gate 123 thereby providing the correct signal for interrupt input 1CA2. Such an interrupt causes each of the inputs 1PB0 to 1PB7 to be scanned in turn to see which of the switches 140 to 147 generated the interrupt.

Furthermore, the pumps connected to sockets 151 and 152 cap generate an alarm signal and a pulse for each drop of insulin or dextrose infused. These signals are applied to interrupt inputs 1CB1, 2CB1, 1CB2, and 2CB2 respectively. In this way the number of drops of both insulin and/or dextrose infused by the pumps is detected by the micro-computer 101 as is an alarm condition in respect of either of the pumps.

Data is also input to the micro-computer 101 by means of the thumbwheel switch 129 previously described for entry of the sample blood glucose level, thumbwheel switch 128 for insertion of the patient factor and thumbwheel switch 127 for insertion of time information.

A 4 bit to 10 bit decoder 110 driven by output lines 2PB4 to 2PB7 respectively selects each thumbwheel switch in turn and the value of each selected thumbwheel switch is read by the input lines 2PB0 to 2PB3 respectively.

It will be apparent that there are four control sequences which are activated by operation of switches 144 to 147 respectively. Operation of switch 147 starts the basal control schedule which sets a default value for the insulin and dextrose infusion pump rates, reads the patient factor from the thumbwheel switch 128 and requests via LED 134, that the operator enter via switch 129 a blood glucose level. Once a blood glucose level is entered via switch 129 the micro-computer 101 uses it to select a pump rate from a look-up table and multiplies the pump rate by the patient factor. Every two hours a new blood glucose level is requested. The pump rates are set at default (i.e. basal) levels until a new value of blood glucose is entered.

The meal schedule runs for three hours after activation of switch 146. A look-up table "contains" the meal profile shown in FIG. 2 and every two minutes a new pump rate is selected from the look-up table depending on the time elapsed since activation of switch 146. The table pump rate is multiplied by the patient factor which is read when the meal schedule is selected.

The hypoglycaemic control schedule is activated by switch 145 and sets the insulin pump rate to 48 drops/min. whilst the dextrose poump rate is set to 1 drop/min. This schedule runs for 1 hour.

At the end of the meal, hypglycaemic and hyperglycaemic control schedules, the basal control schedule starts running.

In addition there are two sub-schedules. The clock sub-schedule reads the initial value of the time from the 4 digit time thumbwheel switch 127. It then services the interrupts coming from input 1CA1 which are generated by the system clock. Thus the correct time is kept in the memory of the micro-computer 101.

The data logging sub-schedule is activated by one of 11 events. They are:

1. Start of BASAL control schedule
2. Start of MEAL schedule
3. Start of HYPOGLYCAEMIC control schedule
4. Start of HYPERGLYCAEMIC control schedule
5. Alarm signal from either of the insulin or dextrose pumps
6. Request for a blood glucose sample
7. Selecting the manual rate for the insulin pump
8. Selecting the manual rate for the dextrose pump
9. Entering a blood glucose level
10. Hourly status
11. Resetting of alarm condition.

The data recorded includes the time of day, identification of the event which initiated the data logging, the current blood glucose level, the time the blood sample was taken, the number of drops of insulin infused, the number of drops of dextrose infused and the current patient factor. When the command P is typed on the teletype and thus entered via line Rx all the events recorded by the data logging sub-schedule are printed. When an R is typed the data logging sub-schedule is reset in order to restart data logging so that memory overflow does not occur in the micro-computer 101.

The details of the integrated circuits illustrated in FIG. 5 are as follows:

| PART NO. | MANUFACTURER | DEVICE NO. | DESCRIPTION |
| --- | --- | --- | --- |
| 101 | MOTOROLA | M68MM01A | Micro-computer |
| 102 | MOTOROLA | MC14020 | 14 Bit Counter |
| 103 | NATIONAL SEMICONDUCTOR | 7441A | 4 Bit - 10 Bit Decoder |
| 104 | NATIONAL SEMICONDUCTOR | 7405 | Hex Inverter |
| 105 | MOTOROLA | MC1488 | Mos to RS232 Converter |
| 106-109 | MOTOROLA | MC14042 | Quad Latch |
| 110 | NATIONAL SEMICONDUCTOR | 7441A | 4 Bit - 10 Bit Decoder |
| 111-114 | FAIRCHILD | 9368 | BCD to 7 Segment Display Driver |
| 115-118 | PLESSEY | GL8R04 | 7 Segment Display |
| 112 | MOTOROLA | MC1489 | RS232 to Mos converter |
| 123 | NATIONAL SEMI- | 74C30 | 8 I/P NAND gate |

| PART NO. | MANU-FACTURER | DEVICE NO. | DESCRIPTION |
|---|---|---|---|
| CONDUCTOR | | | |

The following example illustrates the operation of the apparatus of the preferred embodiment.

EXAMPLE 1

A preplanned meal program for the open loop delivery system was tested. The schedule delivers 7.5 units of insulin over 3 hours in a profile designed (by modelling insulin kinetic data) to stimulate the normal meal insulin response (peak incremental free insulin 78 16 mU/L). The schedule has been implemented on both bedside and portableinsulin delivery systems. Six diabetics were studied for 48 hours on eight occasions; three were normal weight typical insulin-dependent diabetics and three (two obese) were commencing insulin after "tablet failure". For breakfast, lunch and dinner, the peak blood glucose (BG) increments were 2.0, 0.7 (X SE), 1.4, 0.7, 2.0, 0.5 mmol/L and the mean three hour post-prandial increments were 0.5, 0.8, 0.6, 5 and -0.3, 1.0 mmol/L respectively. Exclusion of the two obese subjects made little difference to the mean values after meals although basal BG was higher in the obese subjects (10.0, 0.5 vs. 0.6 0.5 vs. 0.6 0.6 mmol/L). The lunch BG increments were approximately 1 mmol/L less (p 0.05) than those in six diabetics controlled with a closed-loop system where BG changes determined insulin delivery. This difference was attributed to prompt insulin delivery with the open-loop system. The importance of early initiation of insulin delivery for meals was confirmed in three paired studies where a 15 minute delay in the meal schedule resulted in higher one hour post-prandial BG level in each subject (means difference: 1.3 mmol/L). The results demonstrate the practicability of a preplanned meal schedule for control of post-prandial hyperglycaemia and stress the importance of timing of insulin delivery with meals.

The foregoing describes only some embodiments of the present invention and modifications, obvious to those skilled in the art, can be made thereto without departing from the scope of the present invention.

What we claim is:

1. A hybrid open loop/closed loop infusion system comprising an infusion means and a control means connected thereto to control the operation of said infusion means, wherein said infusion means comprises a first pump connected between a first diabetic control liquid reservoir and a tissue access system adapted to be connected to the body of a patient whereby a first diabetic control liquid from said reservoir is infused into said body via said access system; and a second pump connected between a second diabetic control liquid reservoir and said access system whereby a second diabetic control liquid from said second reservoir is infused into said body via said access system; and wherein said control means comprises a basal rate means, a meal rate means, a hyperglycaemic rate means, a hypoglycaemic rate means, a patient blood data entry means and a patient factor entry means; said basal rate means operating said first pump in an open loop mode at a base rate corresponding to an anticipated assessed basal metabolic requirement of said patient, said meal rate means increasing the open loop mode operation of said first pump by predetermined amounts over a predetermined time corresponding to anticipated ingestion of food by, or physical activity of, said patient, said patient blood data entry means being adapted to receive and store patient blood data derived from at least one of a plurality of successive patient blood samplings each taken after an interval of the order of one hour since the previous patient blood sampling and operating said first pump in a quasi-closed loop feedback mode at a first rate dependent upon said blood data but between a predetermined maximum first rate and a predetermined minimum first rate, said patient being able to be infused with safety at said first rate during said interval between successive samplings, said hyperglycaemic rate means operating said first pump at a predetermined hyperglycaemic rate in excess of said predetermined maximum first rate and operating said second pump at a zero or low rate, said hypoglycaemic rate means operating said first pump at a zero rate or a low rate less than said predetermined minimum first rate and operating said second pump at a hypoglycaemic rate, and said patient factor entry means being associated with said data entry means and adapted to receive and store a patient factor which varies from individual patient to individual patient; said predetermined maximum first rate and said predetermined minimum first rate controlled by said data entry means being adjusted by said patient factor entry means in accordance with said patient factor.

2. The system as claimed in claim 1 wherein the rate of operation of said first pump depending upon said blood data is adjusted in accordance with said patient factor.

3. The system as claimed in claim 1 or 2 wherein said patient factor is a numerical constant which multiplies the first pump rates.

4. The system as claimed in claim 1 or 2 wherein said basal rate and said predetermined amounts are adjusted in accordance with said patient factor.

5. The system as claimed in claim 4 wherein said patient factor is a numerical constant which multiplies said basal rate and said predetermined amounts.

6. The system as claimed in claim 1 or 2 wherein said first diabetic control liquid contains insulin.

7. The system as claimed in claim 6 wherein said second diabetic control liquid contains dextrose.

8. The system as claimed in claim 1 or 2 further including means by which intravenous nutrition can be infused to said patient in the form of an infusible solution.

9. The system as claimed in claim 1 or 2 wherein said control means further includes means to sound an alarm when an entry of patient blood data is not received by said patient blood data entry means upon the expiry of said interval.

10. The system as claimed in claim 9 wherein in the absence of an entry of patient blood data into said patient blood data entry means upon the expiration of said interval, the rate of operation of said first pump reverts to said base rate.

* * * * *